(12) United States Patent
Schuh

(10) Patent No.: US 8,187,861 B1
(45) Date of Patent: May 29, 2012

(54) PHOSPHATE REMOVAL-RECOVERY AND BIOFUEL FEEDSTOCK SYSTEM

(76) Inventor: Allen John Schuh, Pleasanton, CA (US)

( * ) Notice: Subject to any disclaimer, the term of this patent is extended or adjusted under 35 U.S.C. 154(b) by 227 days.

(21) Appl. No.: 12/713,734

(22) Filed: Feb. 26, 2010

Related U.S. Application Data

(60) Provisional application No. 61/298,275, filed on Jan. 26, 2010.

(51) Int. Cl.
| | |
|---|---|
| *B01D 11/00* | (2006.01) |
| *B01D 12/00* | (2006.01) |
| *C02F 3/34* | (2006.01) |
| *C02F 9/00* | (2006.01) |
| *C12M 1/00* | (2006.01) |
| *C12N 1/00* | (2006.01) |
| *C12P 1/00* | (2006.01) |
| *D06M 16/00* | (2006.01) |
| *F02M 37/22* | (2006.01) |

(52) U.S. Cl. ............... 435/262; 210/167.01; 210/172.6; 210/243; 210/257.1; 210/511; 210/533; 435/161; 435/162; 435/168; 435/170; 435/171; 435/257.1; 435/259; 435/264; 435/267; 435/289.1; 435/306.1; 435/317.1; 435/946

(58) Field of Classification Search ......................... None
See application file for complete search history.

(56) References Cited

U.S. PATENT DOCUMENTS

| | | | |
|---|---|---|---|
| 4,023,734 | A | 5/1977 | Herve et al. |
| 4,897,266 | A | 1/1990 | Herve et al. |
| 6,346,252 | B1 | 2/2002 | Moigne |
| 7,311,838 | B2 | 12/2007 | Herold et al. |
| 7,419,596 | B2 | 9/2008 | Dueppen et al. |
| 7,431,841 | B2 | 10/2008 | Herold et al. |
| 7,431,952 | B2 | 10/2008 | Bijl et al. |
| 7,435,707 | B2 | 10/2008 | Langer et al. |
| 7,435,715 | B2 | 10/2008 | Broeckx et al. |
| 7,439,034 | B2 | 10/2008 | Weiner et al. |

OTHER PUBLICATIONS

U.S. Dept. Of Energy, Natl. Algal Biofuels Tech. Roadmap, (Jun., 2009) DOE e-Center, https://e-center.doe.gov/iips/faopor.nsf/.../ AlgalBiofuels_Roadmap_7.pdf. See pp. i to iii, 5-8, 12, 15, 21, 48-50, 66, 70, 73-74, 123-124, and 133-134 (total 18 pp.). Entire booklet (214 pp) is attached for completeness.

*Primary Examiner* — Debbie K Ware

(74) *Attorney, Agent, or Firm* — David Pressman

(57) ABSTRACT

For extracting phosphorous from algae-in a body of water, the algae are deposited into a sealable tank (200) that is then evacuated, thereby rupturing the algal cell walls. The ruptured algae are then moved to a second tank (260), mixed with water and bacterial cultures, and allowed to settle until the lipids rise to the top and the oil-less debris settles to the bottom. The second tank also contains sacrificial (295) and rusted electrodes (320). The phosphorous from the algae combines with the rust. The lipids and debris are then removed. Next, an electrical source (315) causes the rust to be removed from the rusted electrodes and settle. In addition, a phosphorous-rich scum floats to the top. These components are placed in storage containers for later use and the water is returned, thereby reducing its phosphorous content.

19 Claims, 2 Drawing Sheets

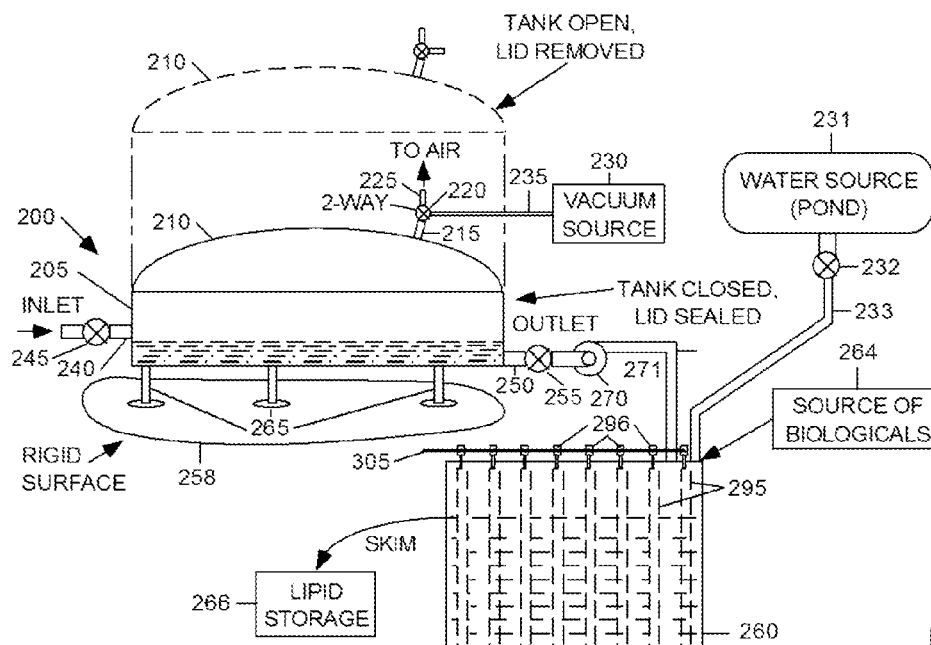
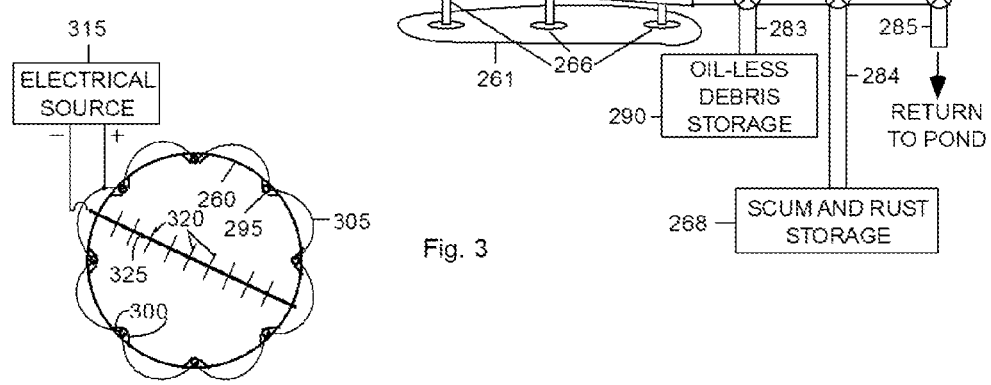
Fig. 2
Fig. 3

PHOSPHATE REMOVAL-RECOVERY AND BIOFUEL FEEDSTOCK SYSTEM

CROSS REFERENCE TO RELATED APPLICATIONS

This application claims priority of my provisional patent application, Ser. No. 61/298,275, filed Jan. 26, 2010. This application is related to application Ser. No. 12/399,323, filed Mar. 6, 2009 now U.S. Pat. No. 8,017,366 and Ser. No. 12/341,380, filed Dec. 22, 2008 now U.S. Pat. No. 8,043,496.

BACKGROUND

1. Field

The field hereof relates to the extraction of substances, and in particular the extraction of phosphate and oil from algae and their water environment.

2. Prior Art

The following is a list of some prior art that presently appears relevant:

| U.S. Pat. No. or Pub. Nr. | Kind Code | Issue or Pub. Date | Patentee or Applicant |
|---|---|---|---|
| 4,023,734 | B1 | May 17, 1977 | Herve et al. |
| 4,897,266 | B1 | Jan. 30, 1990 | Herve et al. |
| 6,346,252 | B1 | Feb. 12, 2002 | Moigne |
| 7,311,838 | B2 | Dec. 25, 2007 | Herold et al. |
| 7,419,596 | B2 | Sep. 02, 2008 | Dueppen et al. |
| 7,431,841 | B2 | Oct. 07, 2008 | Herold et al. |
| 7,431,952 | B2 | Oct. 07, 2008 | Bijl et al. |
| 7,435,707 | B2 | Oct. 14, 2008 | Langer et al. |
| 7,435,715 | B2 | Oct. 14, 2008 | Broeckx et al. |
| 7,439,034 | B2 | Oct. 21, 2008 | Weiner et al. |

Non-Patent Literature: U.S. Dept. of Energy, Natl. Algal Biofuels Tech. Roadmap, (June, 2009).

Phosphorus, a multivalent nonmetal of the nitrogen group, is essential to all life forms. It is essential for the structure of every cell and many biological functions. It is allotropic, i.e., it is capable of existing in two or more distinct forms.

Phosphorus is an integral part of most fertilizers. Concentrated phosphoric acids are used in fertilizers for agriculture and farm production. Fertilizer phosphorus is now primarily derived from phosphorus rocks processed with ammonium nitrate and sulfur. Recovery costs are dependent upon sulfur prices (an oil production byproduct), ammonium nitrate (made with natural gas), and the increased cost to process the decreasing quality of available ore. Since many conditions limit the discovery and exploitation of new sources, it is very desirable that fertilizer makers be able to recover phosphates from local ecosystems for reuse.

In the natural world phosphorous is too active to exist in its pure or elemental form, but only in the form of phosphates, which consists of a phosphorous atom bonded to four oxygen atoms. Phosphates can exist as the negatively charged phosphate ion, which is how they occur in minerals, or as organophosphates in which there are organic molecules attached to one, two, or three of the oxygen atoms. Phosphates can be found in ponds, lakes, and rivers.

Phosphorus moves within the environment mainly through soil, water, and living organisms. Plants absorb and incorporate phosphates from soil. The plants are consumed by herbivores, which are in turn consumed by carnivores. When the carnivores die, their decay returns phosphates to the soil and the process repeats. The movement of phosphorus through the environment is called the phosphorus cycle.

The constant addition of phosphates to the environment by humans conducting agricultural activities causes their concentrations to exceed natural levels, so the phosphorous cycle is strongly disrupted. Phosphorous concentrations have thus been increasing in surface waters, raising the growth of phosphate-dependent organisms, such as algae and duckweed. These organisms use great amounts of oxygen and restrict sunlight from entering the water. This affects the growth cycle of other organisms. The process by which bodies of water become enriched in dissolved nutrients is known as eutrophication; the nutrients stimulate the growth of algae and other plant life and thereby deplete the amount of dissolved oxygen in the water.

The removal of anything from an ecosystem's water is a delicate art. The basic ecological relationships are typically complex. If too much or too little of anything is removed, it can cause a critically deleterious situation. For ecological maintenance ecologists therefore desire to keep phosphorus levels under control in water environments to maintain a natural habitat, while at the same time recovering the excess for other uses. Careful attention is required to leave the originating water environment safe.

Fish excrete phosphorous in their waste materials but the phosphorus can be taken up in part by the plant life and remain in the ecosystem. Excess amounts of phosphorous that would have degraded the environment can be taken up instead by the use of ferric oxide media, which has been shown to remove phosphate from water in a safe, consistent, and repeatable fashion. It is used in aquariums, for example. Typically, in an aquarium setting, after saturation by phosphorus, ferric oxide media is added to collect the excess phosphorus, whereafter the iron particles are removed, discarded, and replaced with new materials.

Ferric oxide media are known by a number of names, including ferric oxide, ferric iron, hematite, red iron oxide, synthetic maghemite, or simply rust. Rust is a general term for a series of iron oxides, usually red oxides, formed by the reaction of iron and oxygen in the presence of water or air moisture. Several forms of rust are distinguishable visually and by spectroscopy, and form under different circumstances including hydrated iron(III) oxides $Fe_2O_3 \cdot H_2O$ and iron(III) oxide-hydroxide ($FeO(OH)$, $Fe(OH)_3$).

In settings other than aquaria, the water containing excess phosphorus is urged to flow through a container and to come into contact with the rust surfaces suspended within it. The surfaces are positioned as baffles. The baffle sheets are sized to equivalently match approximately one gram of rust for each 3.8 liters (1 gallon) of water in the container over a production cycle. The orthophosphate levels in the water can be measured using an appropriate instrument both before and after exposure to rust to help estimate the size of the surfaces necessary in a particular ecological setting. In practice, phosphate levels are measured at the start, and then hourly until levels fail to decline further, which may be in as little as two hours, depending upon water pH and temperature.

Green looking pond water is caused by an excessively large number of phytoplankton, which are part of the algae family that has thousands of distinct species. The algae are distributed worldwide in the sea, in freshwater and in damp situations on land. Algae represent a large group of different organisms from different taxonomic divisions. In general, algae can be referred to as plant-like organisms that are usually photosynthetic and aquatic, but do not have true roots, stems, leaves, or vascular tissue, and have simple reproductive structures. The algae have chlorophyll and can manufacture their own food through the process of photosynthesis. In turn, the algae can be processed to harvest their various components for making fuels and various other useful compounds. These organisms are often very small, with the most common ones found in ponds being around 15 microns in diameter. Algae this small are best processed as described in the above copending '380 application. Algae larger than this are more amenable to bulk processing by the method described below, although the smaller micro-algae will also be processed.

The cell walls of algae are generally the same as those of plants. Different plants have slightly different chemical makeups in their cell walls. A rigid layer of cellulose strengthens the cell and provides structural support. One interesting organic component of the cellulose is lignin, a complex aromatic polymer that provides the primary strength of the cell wall. The cell wall protects the very thin, highly flexible, but structurally weak cytoplasm membrane that lies under the wall and surrounds the interior of the cell.

The cell interior, the cytoplasm, consists of a solution of salts, sugars, amino acids, vitamins, and a wide variety of other soluble materials in water. Since the cytoplasm has a higher solute concentration than the water surrounding the cell, osmosis causes water to pass from outside the cell through the relatively permeable cell wall, continue through the cytoplasm membrane, and dilute the cytoplasm. This builds up pressure within the cell until it equalizes to the effective osmotic pressure and, if not for the rigidity of the cell wall, the cell would burst. Other chemical compounds necessary for the life of the cell are selectively passed through this membrane and waste products are evacuated through it. There are gasses that enter, such as nitrogen, and those that leave, such as oxygen. It is because of the gases in respiration, and the lipids to store energy, that the healthiest of the microscopic algae are normally found at the top layer of the pond water.

SUMMARY

According to one embodiment, a small, portable apparatus provides a systematic process for a low cost, simple, safe, and rapid separation of phosphate from both algae and the ambient water environment. The process is conducted in a manner that is non-polluting to the environment, non-contaminating of feedstock for other uses, and operations can be conducted on a massive scale by a small crew even in remote settings. The apparatus and process improve the economics of producing alternative energy, maintain the ecosystem, and recover excess phosphorus material for other uses.

DRAWINGS

FIG. 2 shows apparatus according to a preferred embodiment.

FIG. 3 is a top view of a tank used in the embodiment of FIG. 2.

Figure 1:
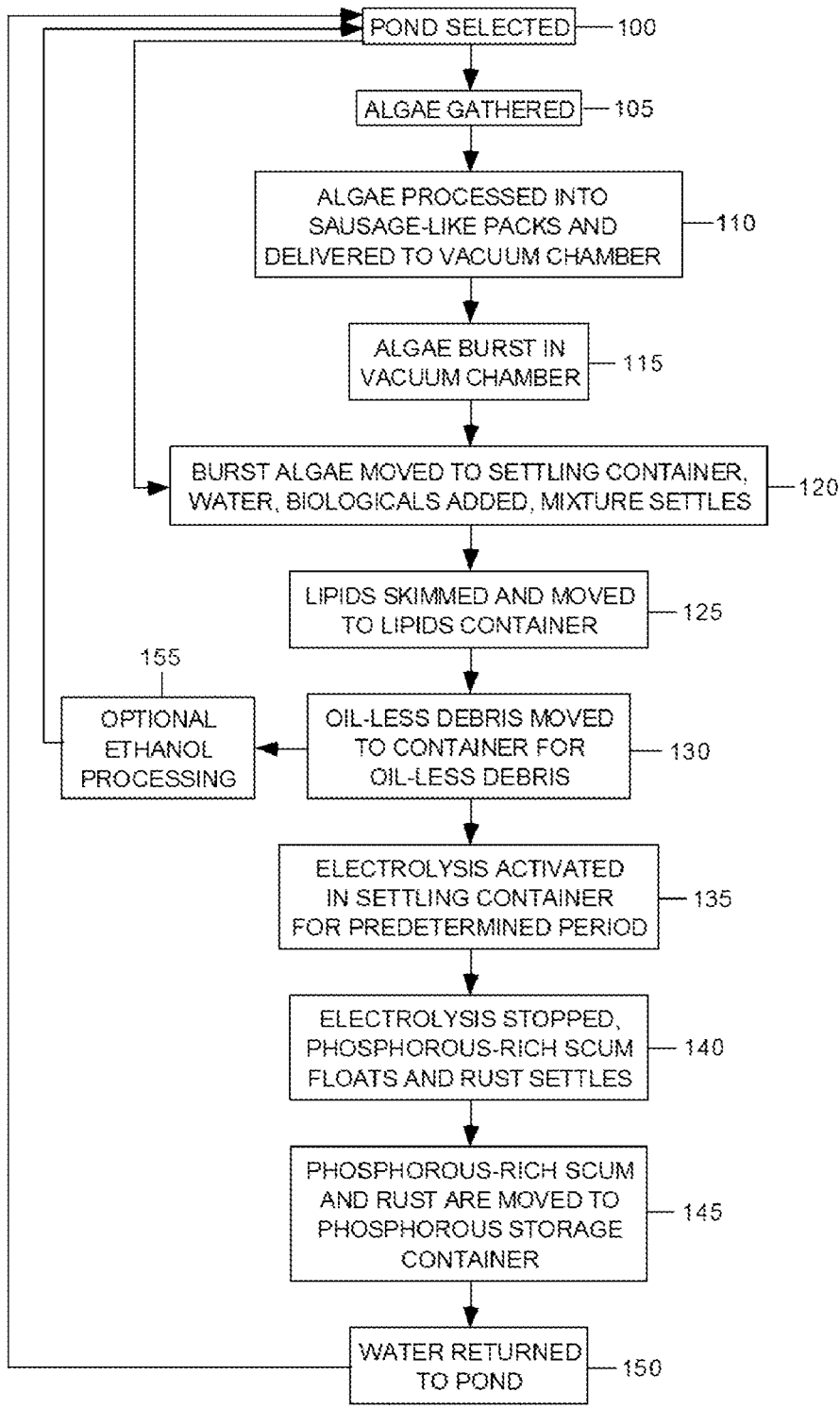
FIG. 1 is a flow diagram illustrating the steps in the procedure for the collection of phosphate and fractionated biofuel feedstock.

| REFERENCE NUMERALS | | | |
| --- | --- | --- | --- |
| 100-155 | Steps | 200 | Vessel |
| 205 | Tank | 210 | Lid |
| 215 | Port | 220 | Valve |

-continued

| REFERENCE NUMERALS | | | |
| --- | --- | --- | --- |
| 225 | Conduit | 230 | Vacuum source |
| 231 | Water source (pond) | 232 | Valve |
| 233 | Conduit | 235 | Conduit |
| 240 | Inlet | 245 | Valve |
| 250 | Outlet | 255 | Valve |
| 258 | Surface | 260 | Tank |
| 261 | Surface | 265 | Legs |
| 266 | Container | 268 | Container |
| 270 | Pump | 271 | Conduit |
| 275 | Conduit | 280 | Valve |
| 281 | Valve | 282 | Valve |
| 283 | Conduit | 284 | Conduit |
| 285 | Conduit | 290 | Container |
| 295 | Electrode | 296 | Connector |
| 300 | Fingers | 305 | Conductor |
| 315 | Source | 320 | Electrode |
| 325 | Conductor | | |

DETAILED DESCRIPTION

First Embodiment—Process Steps—FIG. 1

One key to reaching the resources within the algae relates to establishing a pressure differential to exceed cell wall strength, but perhaps not in the way assumed. If the pressure within the cell expands suddenly relative to the pressure on the outside, then the cell wall will burst like popcorn. Ultimately, the way into the cell is by having its internal pressure exceed the elasticity of the cell wall by exposing the cell to a critical difference between internal and external pressures. If the gas expansion within the cell is sufficient and sudden, the cell wall will have a popcorn-like rupture. Once an algae's cell wall is breached, the resources that were within the call can be more easily recovered.

Algae and its water environment may play a meaningful role in phosphorous recovery if a way is found that is economical, i.e., if a sufficient volume can be processed in a short enough time at a low-enough cost, regardless of the location. E.g., a portable recovery unit can be used and can be delivered by boat, barge, road, rail, or air transportation, especially to remote settings. In such settings, it may be possible to support a small and portable collection station by a flotation device, on the water of the river or pond surface itself, or in an adjacent cove especially constructed for that purpose. In remote settings, where finances for fertilizer acquisition are limited, a method of phosphorus and biofuel feedstock recovery would be most desirable.

There is more than the phosphorus recovery to be gained. Once the cell wall is disrupted, the lipids may float free and to the top of the container for recovery and use as feedstock for biodiesel production. The carbohydrates and other cell debris may drop to the bottom of the container and be selectively recovered for ethanol and methane production. See the copending applications supra. The middle layer of clear water may be returned to the environment. Thus, the process economics of biofuel generation is enhanced by the co-recovery of the feedstock and the fertilizer component.

There is still more at stake than just harvesting algae, recovering phosphorous, and feedstock for biofuel. Ultimately, we want to leave the ecosystem in a healthy and balanced condition, which is better than the way we found it. Proper pond maintenance should keep micro-algae to some minimum where blooms are avoided as they cause fish kill-off and a resulting disagreeable stench to human populations in the area. Removing excess phosphorus means removing the excess over what the existing life forms could process in the current quasi-stationary equilibrium of the pond.

There is another way in which we can help to reestablish the ecosystem: return bio-available carbon to the water, as in converting feedstock to bio-alcohol and releasing it back into the pond. Related is the notion that micro-algae, which cause the kill-off, thrive only where macro-algae populations are insufficient to handle the nitrogen and phosphorous in the water. Thus, giving the pond carbon should help the macro-algae thrive, which in turn is more feedstock for biofuel, but should also proportionally reduce micro-algae populations. It is common practice of aquarium managers to put a few drops of vodka in the tank as a temporary means of controlling micro-algae. Also, the introduction of appropriate bacteria populations can digest micro-algae blooms, making the more rapid return to non-bloom conditions. Once the healthy pond is functioning, the temporary measures will no longer be necessary. The result of these activities should be a sustainable harvest of feedstock and a healthy pond.

FIG. 1 is a flow diagram describing the steps used in phosphate recovery according to a first embodiment, while FIG. 2 shows a suitable apparatus for realizing the steps of FIG. 1. A pond containing sufficient algae for harvesting is selected, step 100. Algae are gathered from the pond, step 105, and processed into sausage-like packs for easy handling and storage, step 110. When it is desired to process the algae, as described below, they are first treated in a vacuum chamber to rupture their cell walls and release their inner contents, step 115. After this treatment, the contents of the vacuum chamber are delivered to a settling and electrolysis tank for further treatment, step 120.

After settling, as described below, lipids (oils) are skimmed and delivered to a container for lipids, step 125, and settled debris is delivered to a container for oil-less debris, step 130. Next, an electrolysis step is activated in the settling and electrolysis tank for a predetermined period of time, step 135. After electrolysis has been stopped, a phosphorous-rich scum layer has formed at the top of the water in the settling container and phosphorus-rich rust has settled to the bottom, step 140.

The scum layer is manually skimmed from the top of the water in the container and the rust is drained from the bottom of the container. These are moved to a phosphorous storage container, step 145, where they can be dispensed for agricultural uses. Next, the water in the settling container is returned to the pond from which it came, step 150.

Optionally, a portion of the oil-less debris can be further processed by methods such as those taught in my above-mentioned pending patent applications to yield, among other things, ethanol. A portion of the ethanol so produced can be delivered back to the pond to retard the growth of micro-algae, step 155.

The above process rectifies the phosphorus cycle in the pond so that macro-algae, i.e., those of diameter greater than 15 microns, flourish. The above process can be repeated indefinitely, as required to maintain a healthy phosphorous level in the pond.

—Apparatus—FIG. 2

FIG. 2 shows apparatus for accomplishing the above process steps according to a preferred embodiment. A first vessel 200 comprises a lower tank portion 205 that has a removable lid 210. Tank 205 is generally cylindrical with a flat bottom. Lid 210 is dome-shaped and sized so that its lower edge mates securely in an airtight fashion with the upper edge of tank 205 when the two are joined together. Clamps and guides (not shown) can be used to ensure that lid 210 remains in its proper, sealing position on tank 205, if desired. Depending upon the size of vessel 200, lid 210 can be lightweight enough to be removed manually or if it is heavy it can be lifted by a crane (not shown).

Lid 210 further includes a port 215 that terminates in a two-way valve 220. In a first position, valve 220 opens port 215 to ambient air through a conduit 225. In a second position, valve 220 connects port 215 to a vacuum source 230 via a conduit 235.

Tank 205 optionally includes an inlet 240 with a valve 245 and an outlet 250 with a valve 255. Inlet 205 can be omitted if tank 205 is filled from above while lid 210 is removed. Tank 205 is supported on a rigid surface 258 by a plurality of footed legs 265 or other means. Alternatively, tank 205 can rest directly on surface 258. The bottom of tank 205 is generally flat and level, although it can be sloped toward outlet 250, if desired.

A second tank 260 is arranged to receive the contents of tank 205 when valve 255 is opened and no vacuum is present in vessel 200. A water source 231, preferably the pond from which the algae are harvested, supplies water to tank 260 via a conduit 233 and a valve 232 when valve 232 is open.

Tank 260 rests on a rigid surface 261, which may or may not be at the same level as surface 258. A plurality of footed legs 266 supports tank 260. If surface 261 is sufficiently lower than surface 258, the contents of tank 205 can flow through outlet 250 and open valve 255 into tank 260 by gravity. Otherwise, an optional pump 270 can be used to move the contents of tank 205 via a conduit 271 into tank 260 at the proper time.

An outlet conduit 275 is located at the bottom of tank 260. Outlet 275 is connected to one-way valves 280, 281, and 282. A storage container for oil-less debris 290 is connected to valve 280 via a conduit 283. A storage container for scum and rust 268 is connected to valve 281 via a conduit 284. A conduit 285 connected to valve 282 returns the contents of tank 260 to pond 231.

Valves 280, 281, and 282 are normally closed and are opened one-at-a-time, as described below. The bottom of tank 260 is optionally sloped to permit all contents of tank 260 to easily exit via conduit 275 at the proper times.

A plurality of electrodes 295 are arranged around the perimeter of tank 260. A connector 296 is affixed to each electrode 295. Connectors 296 can be hanged from above (not shown) in order to support electrodes 295, or electrodes 295 can be captured along the sides of tank 260 by a series of fingers or slots 300 (FIG. 3) that are affixed to the inner surface of tank 260. Fingers or slots 300 do not cover electrodes 295, but are just sufficient to hold electrodes 295 in place while exposing the maximum area of electrodes 295 to the contents of tank 260.

FIG. 3 shows a top view of tank 260 and the arrangement of electrodes 295 and a second set of electrodes 320. All of electrodes 295 are connected together by a conductor 305. Conductor 305 in turn is connected to the positive terminal of an electrical source 315, such as a battery, solar cell array, generator or other direct-current source that can deliver between 12 and 24 volts to the electrical load comprising the contents of tank 260 during electrolysis, as described below. Other voltages are possible.

A second set of electrodes 320 is connected to a second conductor 325. Conductor 325 is connected to the negative terminal of source 315. The length of electrodes 320 is generally equal to the length of electrodes 295, i.e. they extend from the top of tank 260 to the bottom. Electrodes 320 are generally hung from the top of tank 260 so that they can be easily lifted out for cleaning. The combined surface areas of electrodes 295 is preferably about equal to the combined areas of electrodes 320 and the volume of electrodes 295 is preferably greater than the volume of electrodes 320, as explained below.

Tank 205 is preferably made of stainless steel and has diameter and height equal to 1.5 and 0.3 meters, respectively. Tank 205 must be able to hold a mixture of water and algae to a depth of about ⅓ full, and withstand a moderate vacuum of about 0.2 bar. All plumbing fittings attached to vessel 200 are preferably brass, but other materials can be used. Tank 260 preferably holds about 2,000 liters and is made of a nonmetallic, electrically non-conductive material such as plastic. Electrodes 295 and 320 are preferably made of iron that does not contain chromium, zinc or other materials normally used in steelmaking. Such materials can contaminate the contents of tank 260 and may produce compounds that are toxic to algae and animals. Ordinary reinforcing bar used in concrete construction is an ideal material for this use since it is inexpensive and widely available. Electrodes 320 are alternatively made of sheet iron and are deliberately prepared with a layer of rust.

Tank 260 is preferably open at the top. During the electrolysis phase of operation, gaseous oxygen and hydrogen are liberated from the contents of tank 260 and it is necessary that these gases be disposed of by venting into open air in order to prevent the possibility of an explosion. Alternatively, these gases can be disposed of by being captured and retained for another use.

—Operation—FIGS. 1 and 2

The following steps are conducted prior to processing. A pond is selected where algae are plentiful in the aquatic environment and the operators, ecological technicians, or biologists suspect that phosphate levels may be excessive (FIG. 1, step 100). Well-known testing procedures are used to confirm these levels. When the levels are high, a dredge is used to harvest healthy macro and micro-algae that concentrate at the surface of the water (FIG. 1, step 105). After harvesting, the algae are first delivered to a collection station where they are ground and packaged in preparation for processing as discussed below. The ground algae can be wrapped in cheesecloth for ease of handling, if desired. The algae are now ready for processing in the apparatus according to the present embodiment.

Vacuum Treatment

Moist algae are placed in tank 205 (FIG. 1, step 110), the cheesecloth used in transporting them (if any) is removed, and lid 210 is secured on tank 205. Tank 205 is filled about one-third full since the algae will bubble and foam when closed vessel 200 is evacuated. Next, vacuum source 230 is activated and valve 220 is turned to connect pump 230 to vessel 200 (FIG. 1, step 115).

When the pressure within vessel 200 has decreased to about 0.5 bar (about 0.5 atmosphere or 7 psi) and the temperature is about 20° C., the algae cell walls will burst. The operation of pump 230 continues until the pressure within vessel 200 reaches about 0.2 bar in order to ensure that most of the algae walls have burst.

Next, valve 220 is turned so that air is admitted into vessel 200, and vacuum pump 230 is deactivated. When the interior of vessel 200 has reached atmospheric pressure, lid 210 is removed. The operator (not shown) then opens valve 255 and optionally activates pump 270 in order to deliver the contents of tank 205 to tank 260 (FIG. 1, step 120). The operator can use water spray to clean out tank 205 at this time in preparation for vacuum treating another load. Valve 232 is opened to supply water from source 231 to tank 260 via conduit 233. Water is added from source 231 until the contents of tank 260 rise to a level just below the tops of electrodes 295, and below the top of tank 260.

Settling Treatment

At this point, the contents of tank 260 include water and algae with burst cell walls. Although their cell walls are burst, it is still necessary to remove the contents of the algae from their burst cells in order to perform the next steps. A number of biological materials are used to assist in removing the contents. Live, active cultures of bacteria such as *Bifidus lactus, L. acidophilus, L. bulgaricus, L. casei, L. paracasei, L. plantarium, L. rhamnosus*, and *S. thermophilus* are used. These are among the biologicals that produce the enzymes that digest the results of algae blooms in nature and, therefore, are introduced here to dissolve the artificially created algae bloom produced in the controlled conditions of this setting. The desired biological materials are stored in a container 264 for manual addition to tank 260 at the start of the settling step.

After introduction of the biological materials from container 264 to tank 260 and a brief stirring to disperse them, the contents of tank 260 are allowed to rest undisturbed for about two hours (FIG. 1, step 120). During this time, the biological materials will cause the algae to release their contents; these comprise lipids (oils), phosphorous, and the oil-less mash including carbohydrates and proteins.

During the settling process, the contents of tank 260 are in contact with the rusty iron metal comprising electrodes 320. The phosphorus in the contents of tank 260 combines chemically with the rust on electrodes 320. Well-known means (not shown) can be used to measure the phosphorus content in the rust on electrodes 320. When little or no more phosphorus is being collected in the rust, preparation is made for the next step in the process, the treatment by electrolysis.

The lipids, which will have risen to the top of tank 260, are skimmed and stored for another use, such as biodiesel production (FIG. 1, step 125). Oil-less debris comprising cell walls will have settled to the bottom of tank 260 and are delivered through valve 280 to container 290 (FIG. 1, step 130). Valve 280 is open only long enough for the oil-less debris to move from tank 260 to container 290; then it is closed again.

Electrolysis Treatment

After the lipids and oil-less debris have been removed, the water level in tank 260 is brought back to just below the tops of electrodes 295 and 320. Electrolysis will now be used to remove the phosphorus from the rust on the electrodes (FIG. 1, step 135).

Electrolysis is a technique used for removing rust from iron. It is a standard technique well known to tool collectors. It uses the effect of a low voltage direct current and a suitable electrolyte solution. This electrolytic method returns the rusted surface to metallic iron, rust scale is loosened, and can be easily removed along with the phosphorous that has adhered to it. The technique and the solutions used can be selected to be not hazardous. The voltages and currents are low, so there is minimal electrical hazard. The procedure can be conducted in a manner that no noxious fumes are produced. The method is self-limiting in that it is impossible to over-remove either the rust or the phosphorous. When there is no more rust to remove, the reaction stops. If desired, an ionic conductor such as sodium carbonate can be added to the contents of tank 260 in order to increase their electrical conductivity and speed the electrolysis. However, this is usually not necessary.

Source 315 is attached to electrodes 295 and 320, as shown in FIG. 3. Electrodes 295 are connected to the positive terminal of source 315 and electrodes 320 are connected to the negative terminal. Good electrical contact is essential. Multipart objects must have good electrical connections between them. Positive electrodes 295 are sacrificial and will erode over time and need to be replaced. During electrolysis the water, which will eventually be returned to pond 231 (FIG. 1, step 150), will become iron-rich but that is usually a benefit to many plants rather than a problem. Evaporation and electrolysis will deplete some of the water from the container. The lost water can be replaced as needed by temporarily opening valve 232.

When source 315 is turned on, there will soon be a large volume of tiny bubbles in the solution. These bubbles are oxygen and hydrogen and are flammable. Some of the rust and anything attached to it will bubble up to the top and form a cloudy looking layer there. More such material will form on the electrodes. Eventually they will need to be cleaned or replaced. The electrodes give up metal over time. Re-bar (concrete reinforcing bars or rods) are such a good choice for the electrodes as they are inexpensive and easy to acquire in any length. The solution is electrically live. The power must be turned off before making adjustments or placing hands into the solution.

Typical cleaning time for removal of phosphate-bearing rust from electrodes 320 by electrolysis is a few hours. This time depends on the size of the rust surface and of the iron electrode. Visual inspection or manual disturbance by rubbing will provide clues as to the amount of rust remaining. When most of the rust is removed from electrodes 320, source 315 is deactivated and electrolysis stops (FIG. 1, step 140).

The scum material that has risen to the top is skimmed and placed in storage container 268. Then the bottom of tank 260 is opened to flush the remaining phosphorus-rich rust to storage container 268 (FIG. 1, step 145). This phosphorous rich material is ready for agricultural purposes. The remaining water in tank 260 is now returned to pond 231 from which it came (FIG. 1, step 150).

The iron collection surfaces that had rust at the beginning of the collection effort, are now rest free, and may now be returned to a rusty state for the next production run by simply allowing them to be exposed to air under wet or damp conditions. They may be ready for reuse as soon as over night. When exposed to the air, the wet iron surface will acquire surface rust very quickly again.

It is likely that the pond was brought to the attention of the process implementer initially because of a problem with excess of the wrong kind of plant life. The pond maintenance project can be used as part of an overall plan to return it to a healthy state. A healthy pond presents a better opportunity for sustainable harvest of macro-algae for bio-fuel feedstock. An overall plan would show that removal of the excess phosphorous is most efficiently achieved by placing many rust sheet collectors all over the pond to soak up as much material as possible in a short time. This may require employing several extra temporary crews and operating several extra processors just to get the phosphorous levels down to a sustainable replacement level. The crews' only job would be to process the phosphorous by retrieving the many rust surfaces and performing the electrolysis operation on a massive scale.

As the feedstock is harvested and the carbohydrates in the oil-less mash are converted to bio-alcohol, the operators may choose to flush the material back into the pond to provide an ample supply of carbon to complement the nitrogen and phosphorus that are present. The reason the phosphorus is excess is that the plants are not able to process it and the nitrogen because they lack sufficient carbon. Those skilled in the art will find a balance point where the introduction of the ethanol would selectively control the micro-algae by allowing the macro-algae to flourish. Proof of success is that there is never again an algae bloom and fish die-off. The water will look relatively clear. Additionally, there are bacteria that produce enzymes that would help disperse the bloom and minimize its effects if it should occur before achieving ecological balance. The procedure introduced here causes a bloom of sorts under controlled conditions outside the pond. Such bacteria would be introduced as a temporary measure and would remain in the pond at sustainable levels for future use as necessary.

Conclusion, Ramifications, and Scope

Accordingly the reader will see that, according to one or more aspects, I have provided a method and apparatus for removing phosphorous compounds from pond water. The apparatus is relatively small, low cost, simple, safe, and portable. The process is rapid and simple enough to be performed by a small crew of semi-skilled operators, even in remote settings. It will not pollute the environment and will not contaminate feedstock for other uses. The process and apparatus maintain the ecosystem, improve the economics of producing alternative energy, and recover excess phosphorous material for other uses.

While the above description contains many specificities, these should not be construed as limitations on the scope, but as exemplifications of some presently preferred embodiments. Many other ramifications and variations are possible within the teachings. For example, vacuum disruption of the plant cell walls will work with other waterborne or water-rich vegetative matters in addition to algae. Other plants in the pond will contain phosphorous and after the phosphorous removal, they can be used as feedstocks for other processes. For example, cattails also take up phosphorous and they can yield carbohydrates for ethanol production. They can be ground up and used in the same ways as algae. Yeast, fungi, and other micro-biologicals can be used to extract the contents from the burst cells. Selection of the biologicals depends upon their suitability for use in a particular location. A cocktail of biologicals can used initially, then after a few weeks the population of biologicals will adjust to a particular setting. In addition, native and wild strains will appear. All aspects of the preferred embodiments are scalable to any size and to handle any volume of material. Many kinds of vegetative material can be harvested and treated. Instead of manual operation, the operation of the separation system can be automated. Instead of one settling tank, there can be many. In a properly treated pond, aquaculture, the growing of fish and shellfish is possible since the water is cleaned and its acid-base level is properly adjusted. Excretions from the fish will add nitrogen and phosphorous to the pond and contribute to the cycle of harvesting phosphorous from the pond. Besides extracting the phosphorous the combination of several yields is possible, thereby increasing the cost-effectiveness of the project. Electrical energy used to power the vacuum source, pumps, and electrolysis can be at least partially supplied by solar collectors. If the pond is strongly acidic, it can be turned into a source of energy by placing one electrode in the pond and another electrode into the ground nearby, thereby using the pond as a battery with the pond water being an electrolyte. Of course once the pond is properly cleaned the latter option will no longer be viable.

Thus the scope should be determined by the appended claims and their legal equivalents, and not only by the examples given.

The invention claimed is:

1. A method for removing phosphorous from algae, comprising:
providing a body of water containing algae,
collecting at least a portion of said algae from said body of water, and
providing a first tank having a removable, sealable lid and a closed first outlet conduit,
providing a vacuum source,
providing a first valve for selectively connecting said first tank to said vacuum source or to ambient air,
adding said algae to said first tank,
closing said lid,
operating said first valve to connect said first tank to said vacuum source and activating said vacuum source,
evacuating said first tank, thereby bursting the cell walls of said algae,
deactivating said vacuum source and arranging for said first valve to admit ambient air to said first tank,
providing a second tank having a second, closed outlet conduit with second, third, and fourth valves, said valves respectively connected to a storage tank for oil-less debris, a storage tank for scum and rust, and a conduit to said body of water, said second tank also containing sacrificial electrodes and rust-covered electrodes,
opening said first outlet conduit and urging the contents of said first tank to move into said second tank,
providing a source of biological materials that assist in removing the contents of said algae after said walls of said algae are burst,
adding said biological materials to said second tank,
adding sufficient water to nearly fill said second tank,
allowing said algae, said water, and said biological materials to settle for a predetermined period of time so that lipids from said algae float to the top of the contents in said second tank and oil-less debris settles to the bottom of said tank,
skimming said lipids from said top of said contents in said second tank and moving said lipids to a lipid storage container,
temporarily opening said valve connected to said storage tank for oil-less debris so that said debris moves from said second tank into said storage tank for oil-less debris,
providing an electrical source having positive and negative terminals,
connecting said sacrificial electrodes to said positive terminal and said rust-covered electrodes to said negative terminal,
activating said electrical source for a predetermined period of time until the majority of said rust from said rust-covered electrodes has been removed from said rust-covered electrodes and fallen to the bottom of said second container, and a phosphorous-rich scum has gathered at the top of said contents of said second container,
deactivating said electrical source,
skimming said scum and removing said scum to said storage tank for scum and rust,
opening said third valve and permitting said rust at the bottom of said second container to move into said storage tank for scum and rust, and
opening said fourth valve and urging the remaining water in said second tank to return to said body of water,
whereby when said algae are removed from said body of water and treated, said phosphorous content of said body of water is reduced.

2. The method of claim 1 wherein said biological materials are selected from the group consisting of *Bifidus lactus, L. acidophilus, L. bulgaricus, L. casei, L. paracasei, L. plantarium, L. rhamnosus*, and *S. thermophilus*.

3. The method of claim 1, further including processing a portion of said oil-less debris to produce ethanol.

4. The method of claim 3, further including adding said ethanol to said body of water in order to control the growth of micro-algae.

5. A system for removing phosphorous from algae, comprising:
a first tank having a removable, sealable lid and a first outlet conduit,
a vacuum source separate from said first tank,
said sealable lid further including a first valve, said valve arranged to selectively connect said first tank to said vacuum source or to ambient air,
said first tank being arranged to admit and contain water containing algae with an excess of phosphorous, so that when said lid is closed and said first valve connects said first tank to said vacuum source and said vacuum source is activated, said tank is evacuated, thereby creating a vacuum in said first tank which causes the cell walls of said algae to burst,
a second tank arranged to subsequently receive and store for a predetermined period the contents of said first tank after said first valve connects said first tank to said ambient air,
an electrical source having positive and negative terminals, said electrical source being initially inactivated,
said second tank containing a plurality of rusted electrodes and sacrificial electrodes, said rusted electrodes being connected to said negative terminal of said electrical source and arranged to attract and hold phosphorous released from said algae during said predetermined period, said sacrificial electrodes being connected to said positive terminal of said electrical source, so that when said electrical source is activated, said electrodes cause electrolysis to occur in said contents of said second tank, thereby removing said rust and phosphorous from said electrodes,
a plurality of valves and storage containers for containing phosphorous-rich scum and phosphorous-rich rust after said electrical source is deactivated, and
a valve and conduit for releasing said water from said second tank,
whereby when phosphorous, lipids, oil-less debris, and scum from said algae is removed and stored in said storage containers and said water is returned to said pond, the amount of phosphorous in said pond is reduced.

6. The system of claim 5 wherein said first tank further includes an inlet conduit and valve.

7. The system of claim 5, further including a pump for pumping said contents of said first tank from said first tank into said second tank.

8. The system of claim 5, further including a body of water containing algae with an excess of phosphorous and wherein said first tank is coupled to said body of water.

9. The system of claim 5 wherein said second tank is also arranged to receive and store for said predetermined period biologicals that are selected from the group consisting of *Bifidus lactus, L. acidophilus, L. bulgaricus, L. casei, L. paracasei, L. plantarium, L. rhamnosus*, and *S. thermophilus*.

10. The system of claim 5 wherein said oil-less debris is further processed to produce ethanol.

11. A method for removing phosphorous from algae, comprising:
    providing a body of water containing algae,
    collecting at least a portion of said algae from said body of water,
    providing a first tank capable of sustaining a vacuum,
    placing said collected portion of said algae in said first tank,
    providing a source of vacuum connected to said first tank,
    using said source of vacuum to evacuate said first tank until the cell walls of said algae burst,
    providing a source of air and replacing said vacuum in said evacuated first tank with said air,
    providing a second tank capable of holding said algae with said burst cell walls, said second tank also containing sacrificial electrodes and rust-covered electrodes,
    moving said algae with said burst cell walls from said first tank into said second tank,
    adding sufficient water to nearly fill said second tank,
    providing a source of biological materials,
    adding said biological materials to said second tank,
    allowing said algae, said water, and said biological materials in said second tank to settle for a predetermined period of time so that lipids from said algae float to the top of the contents in said second tank, oil-less debris settles to the bottom of said tank, and phosphorous within said contents combines with the rust on said rust-covered electrodes to produce phosphorous-rich rust,
    providing a lipid storage container,
    skimming said lipids from said top of said contents in said second tank and moving said lipids to said lipid storage container,
    providing a storage container for oil-less debris,
    moving said oil-less debris to said storage container for oil-less debris,
    providing an electrical source having positive and negative terminals,
    connecting said sacrificial electrodes to said positive terminal and said rust-covered electrodes to said negative terminal of said electrical source,
    activating said electrical source for a predetermined period of time until the majority of said phosphorous-rich rust from said rust-covered electrodes has been removed from said rust-covered electrodes and fallen to the bottom of said second container, and a phosphorous-rich scum has gathered at the top of said contents of said second container,
    deactivating said electrical source,
    providing a storage container for scum and rust,
    skimming said scum and removing said scum to said storage container for scum and rust,
    moving said phosphorous-rich rust from said bottom of said second tank to said storage container for scum and rust,
    whereby said phosphorous has been removed from said algae and placed in said storage container for said scum and rust thereby reducing the amount of said phosphorous in said water in said second tank, and
    returning the remaining water in said second tank to said body of water,
    thereby reducing the amount of said phosphorous in said body of water.

12. The method of claim 11 wherein said biological materials are selected from the group consisting of *Bifidus lactus, L. acidophilus, L. bulgaricus, L. casei, L. paracasei, L. plantarium, L. rhamnosus,* and *S. thermophilus.*

13. The method of claim 11, further including processing a portion of said oil-less debris to produce ethanol.

14. The method of claim 13, further including adding said ethanol to said body of water in order to control the growth of micro-algae.

15. The method of claim 11 wherein said first tank has a sealable and removable lid.

16. The method of claim 11, further including a conduit and valve between said first tank and said second tank.

17. The method of claim 16 wherein said conduit further includes a pump.

18. The method of claim 11 wherein said first tank is located above said second tank a distance sufficient to permit said contents of said first tank to flow into said second tank under the influence of gravity.

19. The method of claim 11 wherein said electrical source is selected from the group consisting of batteries, solar cell arrays, and generators.

* * * * *